United States Patent
Sakurai et al.

(10) Patent No.: US 8,365,921 B2
(45) Date of Patent: Feb. 5, 2013

(54) CELL SORTING METHOD AND CELL SORTER

(75) Inventors: Takashi Sakurai, Hamamatsu (JP);
Susumu Terakawa, Hamamatsu (JP);
Remi Susuki, Hamamatsu (JP); Hideo Mogami, Hamamatsu (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 617 days.

(21) Appl. No.: 12/561,998

(22) Filed: Sep. 17, 2009

(65) Prior Publication Data
US 2010/0072111 A1 Mar. 25, 2010

Related U.S. Application Data

(63) Continuation-in-part of application No. PCT/JP2008/055126, filed on Mar. 19, 2008.

(30) Foreign Application Priority Data

Mar. 20, 2007 (JP) ................ P2007-073064

(51) Int. Cl.
*B03B 5/00* (2006.01)
*C12Q 1/04* (2006.01)
(52) U.S. Cl. ............ 209/2; 209/3.3; 209/9; 435/325; 435/283.1
(58) Field of Classification Search ............ 209/2, 3.3, 209/9; 435/325, 283.1
See application file for complete search history.

(56) References Cited

U.S. PATENT DOCUMENTS

| | | | | |
|---|---|---|---|---|
| 4,708,799 A | * | 11/1987 | Gerlach et al. | 210/500.23 |
| 4,895,558 A | * | 1/1990 | Cham | 604/5.03 |
| 7,520,159 B2 | * | 4/2009 | Paakkanen et al. | 73/23.37 |

FOREIGN PATENT DOCUMENTS

| | | |
|---|---|---|
| JP | 61265567 | * 11/1986 |
| JP | 3-295464 | 12/1991 |
| JP | 3295464 | 12/1991 |
| JP | 5064578 | 3/1993 |
| JP | 63296686 | 12/1998 |
| JP | 11-133306 | 5/1999 |
| JP | 2006-158611 | 6/2006 |
| JP | 2006-276561 | 10/2006 |
| WO | WO 2008/114828 | 9/2008 |

OTHER PUBLICATIONS

Search Report dated Jun. 10, 2011, for European Patent Application 08722501.7 (filed Mar. 19, 2008), corresponding European regional phase of PCT parent application of the present application, 8 pp.

(Continued)

*Primary Examiner* — Krishnan S Menon
*Assistant Examiner* — Rebecca M Fritchman
(74) *Attorney, Agent, or Firm* — Greenlee Sullivan P.C.

(57) ABSTRACT

To provide a cell sorting method and a cell sorter which are capable of performing sorting focusing on various changes in each cell as stress on living cells is kept as low as possible, and proliferating the sorted cells.
The present invention performs cell sorting using a fiber unit in which a plurality of fibers is bundled so as to be separable and unitable. In the present invention, a cell group containing target cells targeted for sorting is dispersed in a fluid into which the fiber unit is immersed, target fibers to which the target cells are attached among the plurality of fibers, are separated from the fiber unit, and the target cells are proliferated by use of the separated target fibers.

13 Claims, 16 Drawing Sheets

OTHER PUBLICATIONS

International Preliminary Report on Patentability, Corresponding to International Application No. PCT/JP2008/055126, Mailed Oct. 1, 2009.

International Search Report, Corresponding to International Application No. PCT/JP2008/055126, Mailed May 27, 2008.

* cited by examiner

CELL SORTING METHOD AND CELL SORTER

CROSS-REFERENCE TO RELATED APPLICATIONS

This is a continuation-in-part application of application serial no. PCT/JP2008/055126 filed on Mar. 19, 2008, now pending, and incorporated by reference in its entirety.

BACKGROUND OF THE INVENTION

1. Field of the Invention

The present invention relates to a cell sorting method using a fiber unit and a cell sorter having a fiber unit.

2. Related Background Art

A technique of sorting particles such as cells by use of optical fibers is known. With respect to this technique, the following particle sorter is disclosed in Patent Document 1, for example. This particle sorter is configured so that particles serving as sorting targets are floated in a fluid, a focus spot row is formed in the fluid by use of an optical fiber group in which a plurality of optical fibers are arrayed in line, and the particles are sorted focusing on a difference in resistance force on the particles received from the fluid when the optical fiber group is moved to move the focus spot row.

Meanwhile, as a method for performing distinguishing and sorting of living cells, a FACS (fluorescence activated cell sorting) method is known. This FACS method is to measure fluorescence intensities in fluorescently-labeled samples, and to designate arbitrary samples from the obtained intensity distribution data, to perform distinguishing and sorting of living cells.

[Patent Document 1] Japanese Published Unexamined Patent Application No. Hei-03-295464

SUMMARY OF THE INVENTION

However, in a cell sorter to which the FACS method is applied, cells to be sorted are made to flow into a column, and fluorescence intensities are measured at the timing when the cells pass through a predetermined position. Therefore, because it is possible for this kind of cell sorter to measure fluorescence intensities only for an extremely-limited period of time, measurable targets are limited to phenotypes, and it is difficult to detect various changes (for example, a change in color, a change in brightness, a change in contrasting density, temporal changes, and the like in fluorescence or emission) in each cell.

Further, because this kind of cell sorter performs sorting thereof in a state in which cells to be sorted (called samples as well) are floated in a fluid, the cells may deaden in some cases, which leads to high physical invasiveness of the samples.

On the other hand, as a method for sorting samples in, not a floating state, but a still standing state, there is cell trapping and cell cutting by use of a laser scanning method, and the like. However, these methods are greatly dependent on artificial judgment in the selection of an area targeted for sorting or the like, and it is difficult to automate those methods.

Further, in order to proliferate samples which are unified (cloned) by a culture or the like, it is necessary to add another operation such that a sorted clone is conveyed to an appropriate place, or the like.

In this way, conventionally, there is no preferred method capable of performing a series of operations for performing sorting thereof focusing on various changes in each cell as stress on living cells is kept as low as possible, to proliferate the sorted cells.

Then, the present invention was made to solve the above problems, and it is an object of the present invention to provide a cell sorting method and a cell sorter capable of performing sorting thereof focusing on various changes in each cell as stress on living cells is kept as low as possible, and proliferating the sorted cells.

Means for Solving the Problem

In order to achieve the object, a cell sorting method using a fiber unit in which a plurality of fibers are bundled so as to be separable and unitable, the cell sorting method of the present invention includes the processes of dispersing a cell group containing target cells targeted for sorting in a fluid into which the fiber unit is immersed, separating target fibers to which the target cells are attached among the plurality of fibers, from the fiber unit, and proliferating the target cells by use of the separated target fibers.

In this cell sorting method, the fiber unit in which the plurality of fibers are bundled so as to be separable and unitable is used. Therefore, it is possible to separate the cells that remain attached to the fibers, and further, the cells are unitized into each fiber. Further, the optical characteristics of the respective cells are measured through the fibers, and the respective cells are sorted in accordance with the optical characteristics.

Further, in the cell sorting method, it is preferable that other fibers to which cells are not attached are arranged around the target fibers in proliferating the target cells.

According to this aspect, a fiber group for obtaining a cell group of the target cells whose characteristics such as functions and morphology are unified is formed from the separated fibers and the other fibers.

Moreover, in the cell sorting method, it is preferable that, before separating the target fibers from the fiber unit, the non-target cells are removed from non-target fibers to which non-target cells which are not targeted for sorting are attached or close among the plurality of fibers.

According to this aspect, only necessary samples preferentially remain in large amounts by removing the non-target cells.

Further, before separating the target fibers from the fiber unit, optical characteristics of light taken out of the fiber unit may be measured, and the target fiber may be separated on the basis of the measured optical characteristics.

According to this aspect, the cells are sorted on the basis of the functions and morphology of the target cells which has taken time to measure.

Then, the present invention provides a cell sorting method using a fiber unit in which a plurality of fibers are bundled so as to be separable and unitable, the cell sorting method of the present invention including the processes of dispersing a cell group containing target cells targeted for sorting in a fluid into which the fiber unit is immersed, removing the non-target cells from non-target fibers to which non-target cells which are not targeted for sorting are attached or close among the plurality of fibers, and thereafter, proliferating the target cells by use of the fiber unit.

According to this cell sorting method as well, the fiber unit is used. Therefore, it is possible to separate the cells that remain attached to the fibers, and further, the cells are unitized into each fiber. Further, the optical characteristics of the respective cells are measured through the fibers, and the respective cells are sorted in accordance with the optical characteristics. After removing the non-target cells, some of the samples may be picked up. However, when an attempt is made to continue an operation using the fiber unit such as proliferating the target cells, the operation may be continued without separating the optical fibers. In this way, in this method, it is possible to obtain the cells with high efficiency by multiplying arbitrary cells or the like. Therefore, it is possible to exert an advantageous effect even in the case in which the number of necessary cells contained in initial samples is in an extremely minute amount.

Further, the present invention provides a cell sorting method using a fiber unit in which a plurality of fibers are bundled so as to be separable and unitable, the cell sorting method including the processes of respectively allocating coordinates to the fibers forming the fiber unit; dispersing a cell group containing target cells targeted for sorting in a fluid into which the fiber unit is immersed, designating the coordinates allocated to target fibers to which the target cells are attached among the plurality of fibers, separating the target fibers whose coordinates are designated, from the fiber unit, and proliferating the target cells by use of the separated target fibers.

In this cell sorting method, the target fibers specified by designating the coordinates are separated, and the target cells are proliferated by use of the separated target fibers.

In this cell sorting method, wherein, it is preferable that, before designating the coordinates allocated to the target fibers, the non-target cells are removed from non-target fibers to which non-target cells which are not targeted for sorting are attached or close among the plurality of fibers.

According to this aspect, only necessary samples preferentially remain in large amounts by removing the non-target cells.

Then, when removing the non-target cells from the non-target fibers, a light is applied to the non-target fibers to induce a reduction in adhesive force between the non-target cells and the optical fibers, which makes it possible to cause damage to the non-target cells or deaden the non-target cells.

Moreover, the present invention provides a cell sorter including a fiber unit in which a plurality of fibers are bundled so as to be separable and unitable, and coordinates are respectively allocated to the fibers, and a measuring device that measures optical characteristics of light acquired from the fiber unit.

In this cell sorter, the fiber unit in which the plurality of fibers are bundled so as to be separable and unitable is used. Therefore, it is possible to separate the cells that remain attached to the fibers, and further, the cells are unitized into each fiber. Further, the optical characteristics of the respective cells are measured through the fibers by the measuring device, and the respective cells are sorted in accordance with the optical characteristics.

Further, it is preferable that the cell sorter further includes coordinate specifying means for specifying the coordinates allocated to target fibers to which target cells targeted for sorting are attached among the coordinates allocated to the plurality of fibers.

In this cell sorter, the target fibers whose coordinates are specified by the coordinate specifying means are separated, and the target cells are proliferated by use of the separated target fibers.

Effect of the Invention

As described above in detail, in accordance with the present invention, it is possible to obtain a cell sorting method and a cell sorter which are capable of performing sorting focusing on various changes in each cell as stress on living cells is kept as low as possible, and proliferating the sorted cells.

BRIEF DESCRIPTION OF THE DRAWINGS

FIG. 13A is a spectrum distribution in which a particular wavelength is intense, and FIG. 13B is a spectrum distribution which is gentle as a whole.

FIG. 14A shows a case in which there is no temporal change in brightness, and FIG. 14B shows a case in which there are temporal changes in brightness.

DESCRIPTION OF THE REFERENCE NUMERALS

1 . . . Cell sorter, 2 . . . Fiber unit, 3 . . . Housing container, 4 . . . Controller, 5 . . . Measuring device, 5*a* . . . Wavelength selecting part, 5*c* . . . Imaging unit, 6 . . . Optical fiber, 8 . . . Fiber separating part, 10 . . . Cell group, 11 . . . Target cell, 12 . . . Non-target cell, 61, 62, 63, 64, 65 . . . Optical fiber

DESCRIPTION OF THE PREFERRED EMBODIMENTS

Hereinafter, an embodiment of the present invention will be described. In addition, the same reference symbol is used for the same element, and an overlapping description thereof will be omitted.

Figure 1:
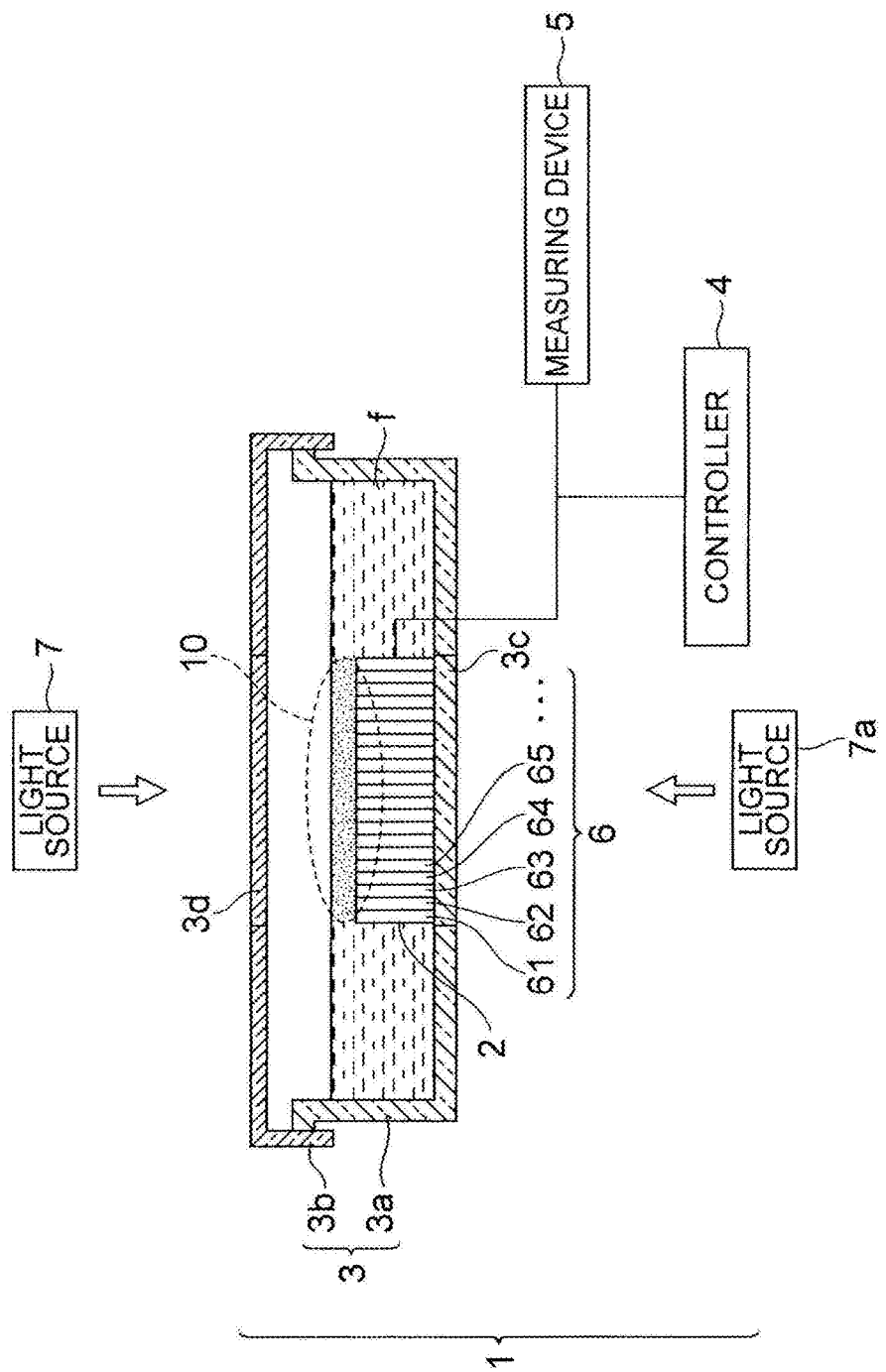
FIG. 1 is a diagram schematically showing a configuration of a cell sorter used for a cell sorting method according to an embodiment of the present invention.

FIG. 1 is a diagram schematically showing a configuration of a cell sorter 1 used for a cell sorting method according to the embodiment of the present invention. The cell sorter 1 has a fiber unit 2, a housing container 3, a controller 4, and a measuring device 5.

Figure 2:
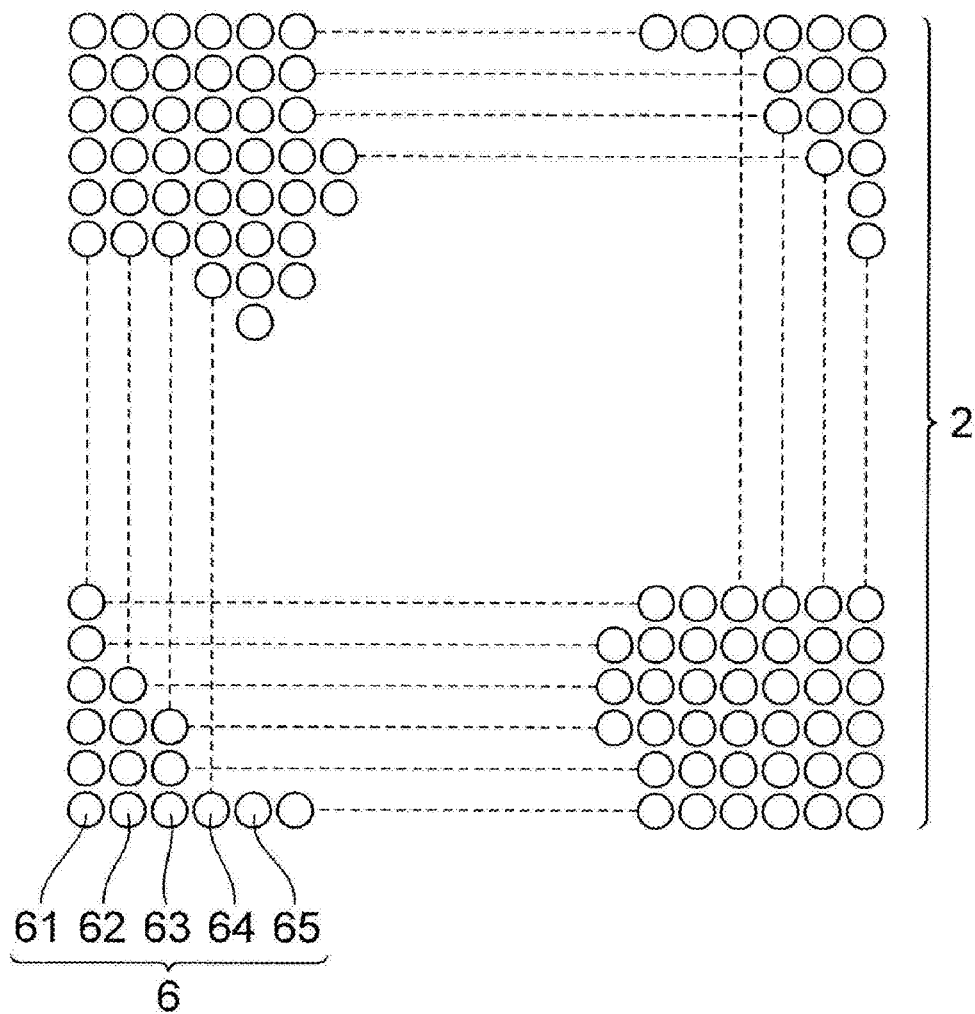
FIG. 2 is a plan view schematically showing a fiber unit.

The fiber unit 2 is, as shown in detail in FIG. 2, configured so that a plurality of optical fibers 6 (61, 62, 63, 64, 65, and . . . ) are arranged in a grid (in a matrix) with regularity vertically and horizontally, and is contained in the housing container 3 so that the end faces of the respective optical fibers 6 face to the top and bottom sides.

This fiber unit 2 is configured so that the optical fibers 6 (61, 62, 63, 64, 65, and . . . ) are integrated by use of light-sensitive resin or the like. The fiber unit 2 is allowed to be divided into each of the respective optical fibers 61, 62, 63, 64, 65, and . . . or united due to melting or curing of the optical sensitive resin, and the optical fibers 6 are bundled so as to be separable and unitable. When the fiber unit 2 is divided into each of the respective optical fibers 61, 62, 63, 64, and 65, the respective optical fibers 6 can be individually taken out to the outside of the housing container 3. Further, the optical sensitive resin can be used as a coupling agent between the optical fibers 6 and cells.

Moreover, in the fiber unit 2, coordinates are allocated to the respective optical fibers 61, 62, 63, 64, 65, and . . . . Then, in the cell sorter 1, it is possible to specify the coordinates of the respective optical fibers 6 by use of the controller 4, and it is possible to separate the optical fibers 6 having specified coordinates individually to take those out therefrom (the details will be described later).

In addition, the optical fibers 6 may be composed of silica optical fiber, plastic optical fiber, multicomponent glass fiber, or the like, and the material thereof is not especially limited. The optical fibers 6 have a core diameter of approximately 3 to 10 microns in diameter, that are set to an appropriate length in order not to cause bending and the like when the fiber unit 2 is divided to individually take those out.

The housing container 3 is composed of a container main body part 3a and a lid part 3b, and has a size in which a fluid "f" for floating cells after the fiber unit 2 is placed on the base of the container main body part 3a.

The container main body part 3a is made of resin, glass, or the like, and at least a predetermined range in its central portion is a transmissive area 3c through which light is allowed to transmit. The lid part 3b as well is made of resin, glass, or the like in the same way as the container main body part 3a, and at least a predetermined range in its central portion is a transmissive area 3d through which light is allowed to transmit.

Then, the housing container 3 is covered with the lid part 3b in a state in which the fiber unit 2 and the fluid "f" are contained in the container main body part 3a, and the fiber unit 2 is in a state of being immersed in the fluid "f" (in addition, FIG. 1 shows a state in which a cell group 10 is dispersed).

The controller 4 has at least a CPU, a ROM, and a RAM, and the CPU operates in accordance with a control program stored in the ROM. Then, while the controller 4 controls a measuring operation by the measuring device 5, the controller 4 specifies coordinates of the optical fibers 6.

The measuring device 5 detects fluorescence (excited from the bottom face side of the optical fibers 6 by a light source 7a or the like) and luminescence emitted from the cells attached to the optical fibers 6, transmitted light output from a light source 7 to transmit through the fiber unit 2, to measure the functions and morphology of the cells which are attached or close to the optical fibers 6. Further, although not shown in the drawing, the measuring device 5 displays an image or a graph showing a measured result on a predetermined display.

Figure 3:
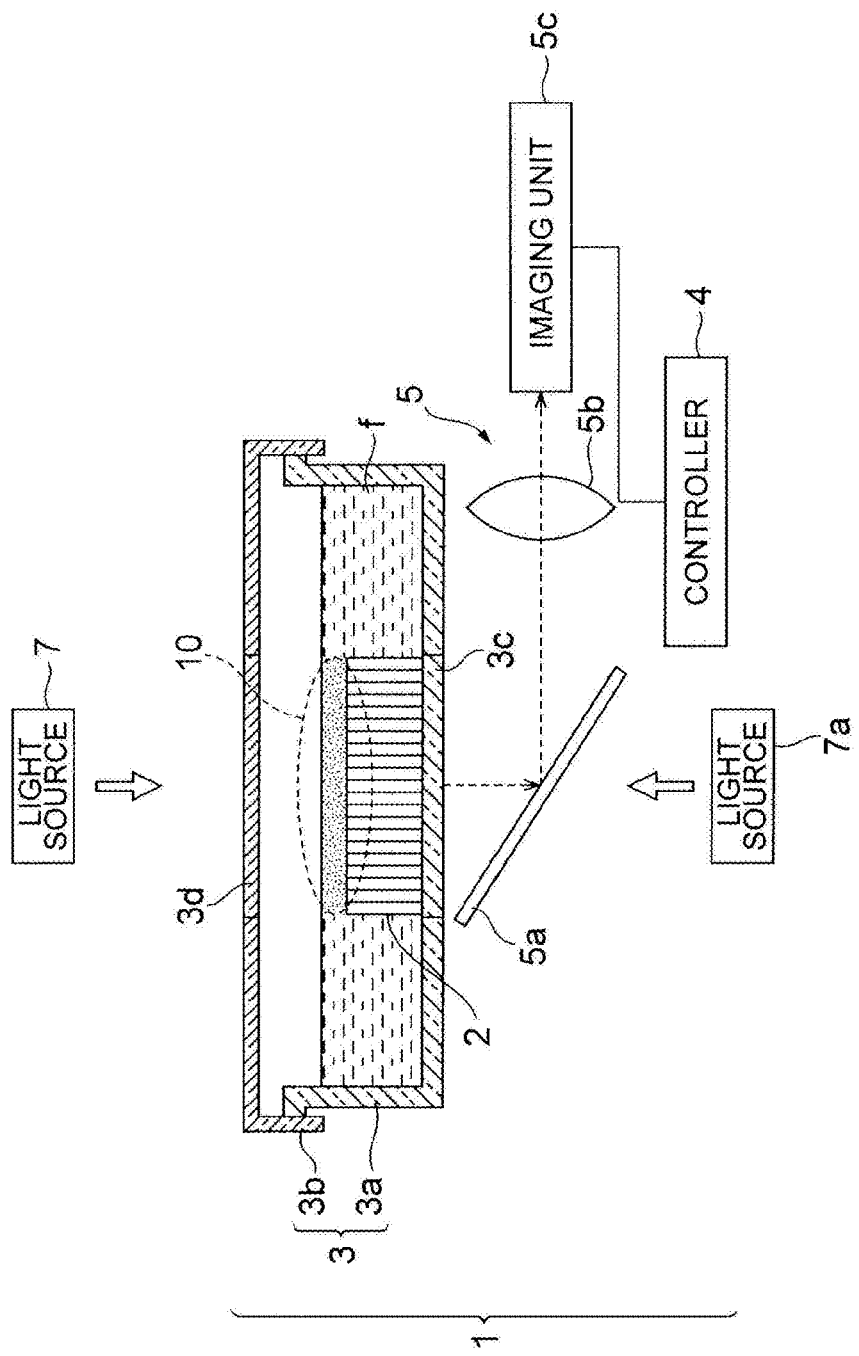
FIG. 3 is a diagram showing the configuration of the cell sorter of FIG. 1 in more detail.

Here, in FIG. 3, a detailed configuration of the measuring device 5 is shown. As shown in the drawing, the measuring device 5 is composed of a wavelength selecting part 5a composed of a dichroic mirror or the like, an imaging lens 5b, and an imaging unit 5c. The wavelength selecting part 5a allows a wavelength component of an excitation light applied from the light source 7a provided below the container main body part 3a toward the end of the fiber unit 2, to directly transmit through, and reflects a wavelength component of fluorescence, luminescence, or transmitted light transmitting through the transmissive area 3c of the container main body part 3a from the optical fiber unit 2, toward the imaging lens 5b. That is, the wavelength selecting part 5a is provided for separating an excitation light from the light source 7a and light from the cells attached to the optical fiber unit 2. Further, the imaging lens 5b forms a two-dimensional image of fluorescence, luminescence, or transmitted light transmitting through the optical fibers 6 forming the optical fiber unit 2, on an imaging area of the imaging unit 5c. The imaging unit 5c takes the formed two-dimensional image to generate image data, and analyzes color components and brightness of an image for each of the plurality of optical fibers 6 with reference to the image data, to measure the functions and morphology of the cells attached to the respective optical fibers. Then, the imaging unit 5c transmits a measured result of each optical fiber measured, to the controller 4.

Figure 4:
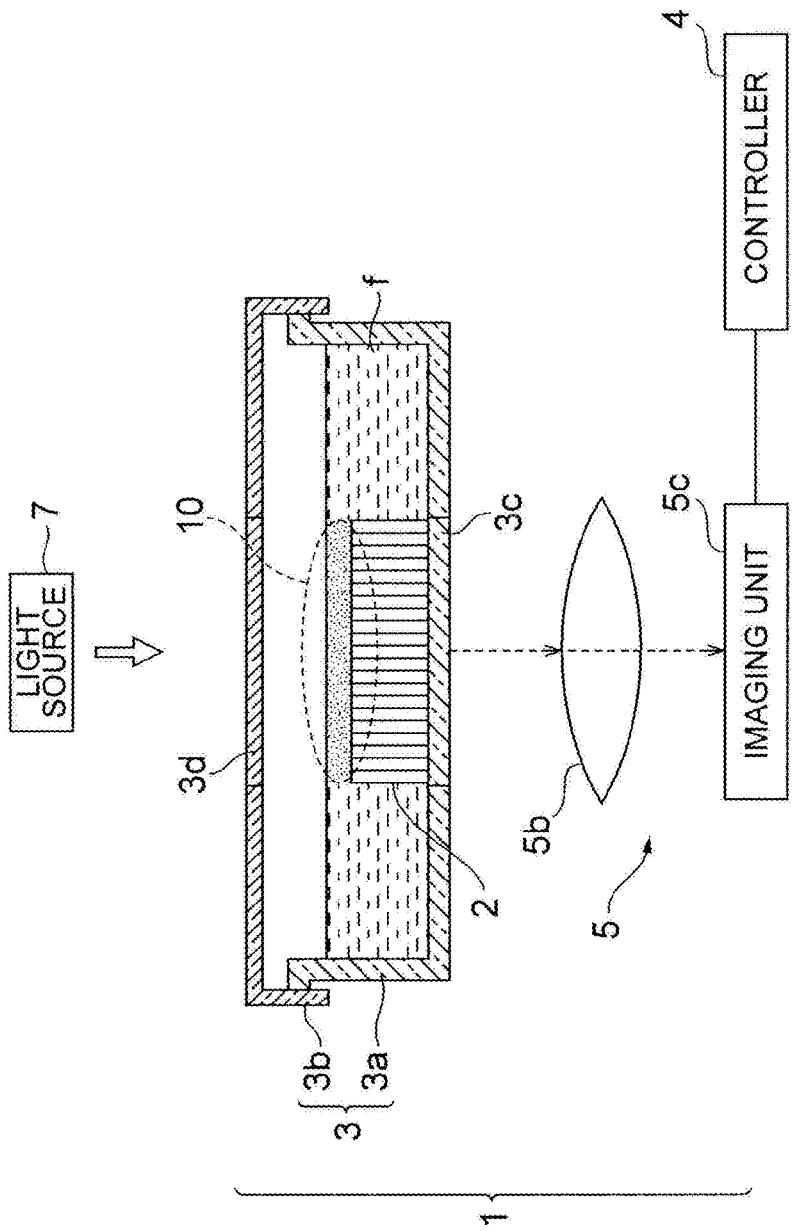
FIG. 4 is a diagram showing another configuration of the cell sorter of FIG. 3.

In FIG. 4, another configuration of the measuring device 5 is shown. As shown in the drawing, luminescence or transmitted light transmitting through the transmissive area 3c of the container main body part 3a from the optical fiber unit 2 may not be separated by a dichroic mirror, but directly guided to the imaging unit 5c via the imaging lens 5b.

(Content of Cell Sorting Method)

Next, a cell sorting method by use of the cell sorter 1 having the above-described configuration will be described with reference to FIGS. 5 to 7. This cell sorting method may be achieved by a sorting procedure A shown hereinafter, and may also be achieved by a sorting procedure B.

Figure 7:
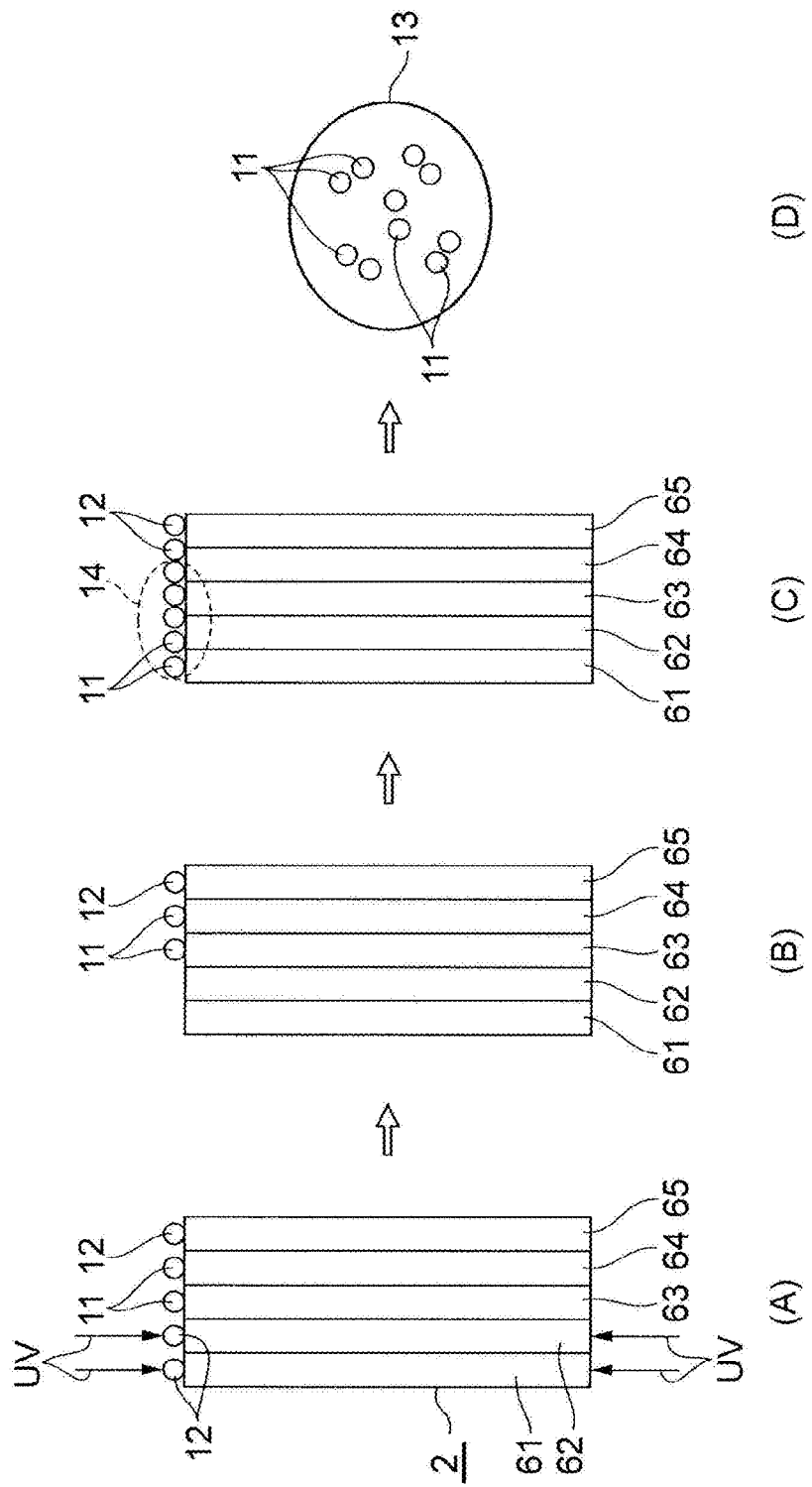
FIG. 7 are diagrams schematically showing a cell sorting procedure according to a sorting procedure B.
Figure 8:
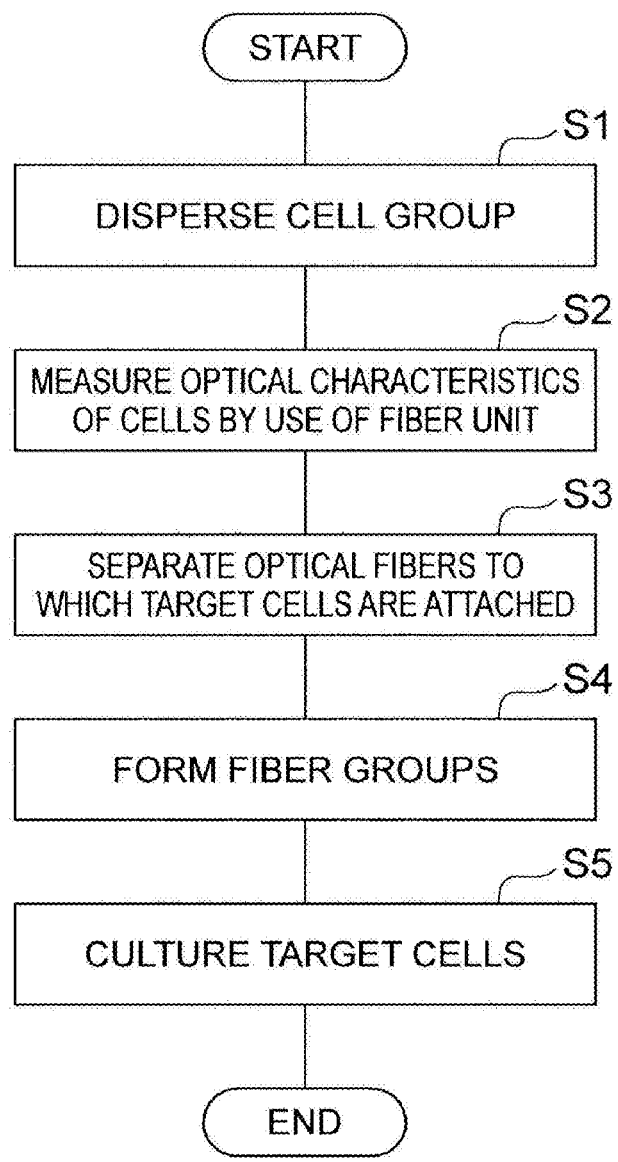
FIG. 8 is a flowchart showing the sorting procedure A.
Figure 9:
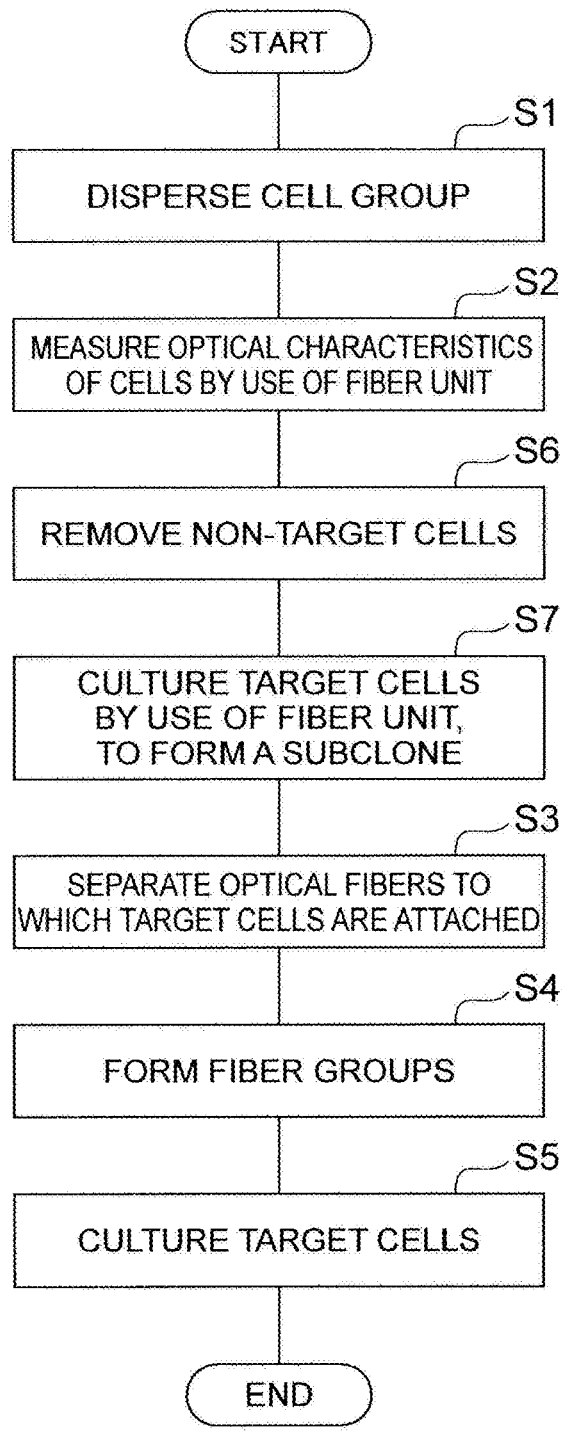
FIG. 9 is a flowchart showing the sorting procedure B.

Although the details will be described later, the sorting procedure A is a procedure for sorting cells by use of the fiber unit 2, and the sorting procedure B is a sorting procedure in the case in which cells are sorted after carrying out the removal (trimming) of unnecessary cells. In addition, FIG. 5 is a front view showing the fiber unit 2 to which the cells are attached. FIG. 6 are diagrams schematically showing a cell sorting procedure according to the sorting procedure A, and FIG. 7 are diagrams schematically showing a cell sorting procedure according to the sorting procedure B. Moreover, FIG. 8 is a flowchart showing the sorting procedure A, and FIG. 9 is a flowchart showing the sorting procedure B. In addition, the steps are abbreviated as S in FIGS. 8 and 9.

(With Respect to Sorting Procedure A)

First, the lid part 3b of the housing container 3 is removed, and the cell group 10 is dispersed in the fluid "f" contained in the container main body part 3a (S1). The cell group 10 contains not only target cells (or a cell group) 11 targeted for sorting, but also the other cells (cells which are not targeted for sorting, and hereinafter called "non-target cells") 12.

In addition, the respective cells may be unstained cells, and may use fluorescent molecules, luminescent probes, or the like as labels, thereby allowing various measurements of optical characteristics or functions of the cells. Excitation and detection of fluorescent molecules used as labels are performed by use of the fiber unit 2, and it takes time necessary to determine changes in the morphology and functions of the cells on the basis of temporal changes in fluorescence intensity thereof.

Figure 5:
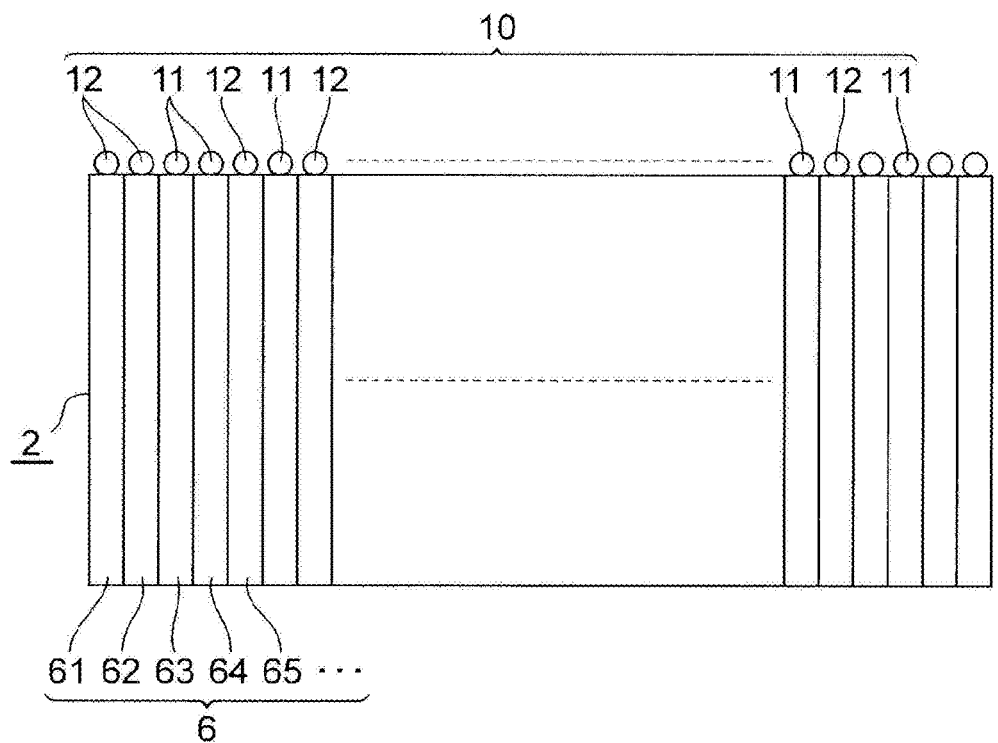
FIG. 5 is a front view showing the fiber unit to which cells are attached.

Then, as shown in FIG. 5, the target cells 11 or the non-target cells 12 are attached to the end faces of the respective optical fibers 61, 62, 63, 64, 65, and . . . of the fiber unit 2. In this case, the target cells 11 or the non-target cells 12 are attached to the upper side end faces of the respective optical fibers 61, 62, 63, 64, 65, and ..., meanwhile, those are merely located very near (close to) the end faces of the respective optical fibers 61, 62, 63, 64, 65, and ... in some cases, and those are attached astride to a plurality of optical fibers in some cases.

Next, because it takes time necessary to measure the morphology and functions of the respective cells, lights acquired from the fiber unit 2 are taken into the measuring device 5, and their optical characteristics are measured by the measuring device 5 (S2). Although the details will be described later, for example, a light is applied from the light source 7, and the transmitted light transmitting through the fiber unit 2 is taken into the measuring device 5, to photograph a transmission image. Further, it takes a certain amount of time to measure brightness, intensity, and the like of luminescence and fluorescence emitted from the respective cells by the measuring device 5.

Figure 6:
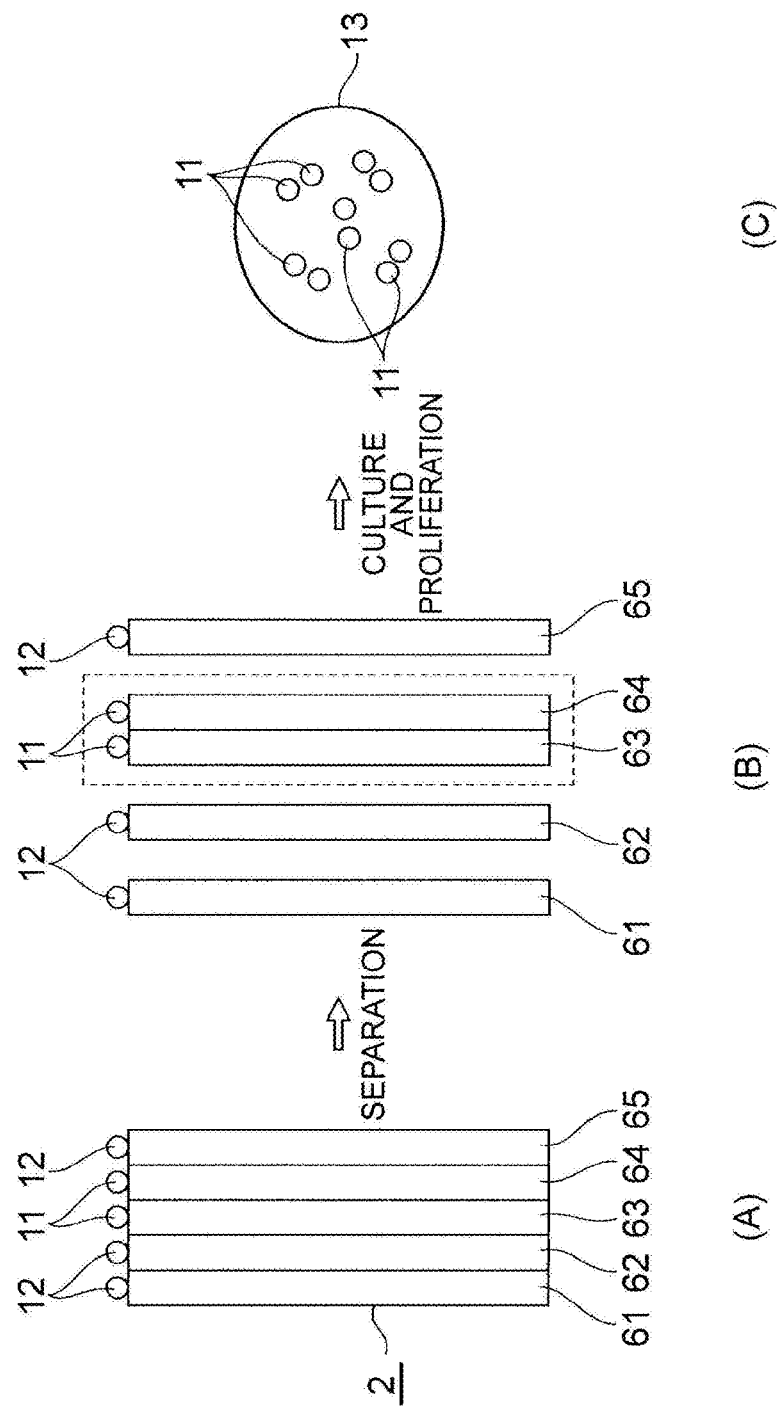
FIG. 6 are diagrams schematically showing a cell sorting procedure according to a sorting procedure A.

Next, as shown in FIGS. 6A and 6B, a predetermined light is applied to melt the light-sensitive resin, and the fiber unit 2 is divided into each of the optical fibers 6 (the respective optical fibers 61, 62, 63, 64, and 65 are discretely separated). Thereafter, the optical fibers to which the target cells 11 are attached (the optical fibers 63 and 64 in the case of FIG. 6, which are called target fibers as well) among the optical fibers 6 are separated therefrom on the basis of the optical characteristics measured in S2, to be taken out to the outside of the housing container 3 (S3).

In addition, in FIG. 6, only the optical fibers 61, 62, 63, 64, and 65 among the optical fibers 6 in the fiber unit 2 are shown. In FIG. 6A, the optical fibers 61, 62, 63, 64, and 65 to which the target cells 11 or the non-target cells 12 are attached are shown. In FIG. 6, the target cells 11 are attached to the optical fibers 63 and 64, and the non-target cells 12 are attached to the optical fibers 61, 62, and 65. Further, in FIG. 6B, the optical fibers 63 and 64 to be taken out are surrounded by the dotted line.

Here, at the time of separating the optical fibers 63 and 64 in S3, an operator may designate the positions (or the coordinates) of the optical fibers 63 and 64 on the basis of the measured result in S2. However, the controller 4 may specify the coordinates of the optical fibers 63 and 64 in accordance with an input operation (for example, an input operation by a keyboard and/or a mouse) carried out by an operator while viewing an image showing the measured result in S2, and the coordinates thereof may be designated on the basis of the result.

In this case, the controller 4 has the function as coordinate specifying means for specifying the coordinates of the optical fibers to which the target cells are attached. In this way, because automation of sorting for automatically separating optical fibers without manpower is facilitated, the cell sorting method is simplified, which makes it possible to easily sort the cells.

Next, the optical fibers 6 (the optical fibers 63 and 64) separated in S3 are collected, and other optical fibers to which cells are not attached are arranged around the optical fibers 63 and 64, to form a fiber group 13 in which those are united as shown in FIG. 6C. This fiber group 13 is used for acquiring a cell group of the target cells 11 whose characteristics such as functions, morphology, and the like are unified (cloned) by culturing the target cells 11. However, after other optical fibers to which cells are not attached are arranged around the optical fibers 6 (the optical fibers 63 and 64), those may be put together with light-sensitive resin (by curing the light-sensitive resin), to configure the fiber unit 2 again.

Then, the target cells 11 are cultured by use of the fiber group 13 formed in S4 (S5). The cell sorting method according to the sorting procedure A is terminated as described above.

As described above, in the cell sorting method according to the sorting procedure A, sorting is not performed in a state in which cells are merely floated, but is performed under the condition that cells are attached to the optical fibers 6 in the fiber unit 2 and there is no time restriction. Therefore, stress such as death or damage to living cells is remarkably reduced, which makes it possible to sort cells with a minimum of such stress.

Further, because the fiber unit 2 is used, it is possible to measure the functions and morphology of cells to be sorted in accordance with optical characteristics of light acquired from the fiber unit 2, and it is possible to spend the necessary time to measure the functions and morphology of the cells.

Therefore, by measuring optical characteristics with the measuring device 4 in S2, it is possible to separate the optical fibers 6 on the basis of the measured optical characteristics in the following S3. Accordingly, in the cell sorting method according to the sorting procedure A, it is possible to perform sorting focusing on various changes in the function and morphology of each cell.

Then, it is possible to sort cells on the basis of their responsiveness (time-series changes). Therefore, it is possible to expect purification of a pancreatic beta cell line with not only a great insulin contain, but also high glucose responsiveness. Therefore, the cell sorting method according to the sorting procedure A leads to the acquisition of higher-quality cells, that is effective for the development of an artificial organ.

Moreover, it is possible to take time to identify and sort cancer cells unresponsive to anticancer drugs by morphology and function. Therefore, the cell sorting method according to the sorting procedure A can be used for determination of an effect thereof when a novel anticancer drug is created, which makes it possible to identify and collect cells with higher precision. Accordingly, in the cell sorting method according to the sorting procedure A, it is possible to flexibly respond to a selection of a chemical compound to be followed up in drug discovery screening, which makes it possible to respond to a greater variety of cell function searches.

Further, because the respective optical fibers 6 are bundled so as to be separable and unitable in the fiber unit 2, it is possible to separate desired optical fibers 6 from the other optical fibers 6, to take those out. Therefore, only the optical fibers 6 to which target cells targeted for sorting are attached can be separated to be taken out, and target cells can be proliferated by use of the optical fibers 6.

Additionally, because the fiber unit 2 is used in the sorting procedure A, the respective cells are to be unitized by the optical fibers 6. Accordingly, not only is it easy to distinguish the respective cells, but also it is possible to specify the positions of the cells in accordance with the positions of the optical fibers 6, which makes it possible to simply and reliably specify and sort the cells. Additionally, because the respective coordinates are allocated to the respective optical fibers 6, provided that the coordinates are specified, it is possible to specify desired optical fibers, which makes it possible to easily find out the positions of a plurality of the optical fibers 6.

(With Respect to Sorting Procedure B)

In the sorting procedure A, it is necessary to sort the target cells 11 from among many cell groups at the time of separating the optical fibers, and the sorting may be difficult in some cases. Further, even if only the target cells 11 are sorted, the non-target cells 12 may be mixed therein for some reason in some cases. In order to accurately respond to such a situation, it is preferable to remove unnecessary cells in accordance with the sorting procedure B as shown in FIG. 7. The cell sorting according to the sorting procedure B is performed in accordance with the flowchart shown in FIG. 9. In addition, as shown in FIG. 9, the cell sorting according to the sorting procedure B is different from the cell sorting according to the sorting procedure A in the point that S6 and S7 are added between S2 and S3, and the other points are the same.

Then, in the cell sorting according to the sorting procedure B, as shown in FIGS. 7A and 7B, the removal of the non-target cells 12 is performed with respect to the fiber unit 2 (S6). In this case, for example, ultraviolet light UV or a light into which a labeled pigment is absorbed is applied from the light source 7 to the non-target cells 12, to deaden the non-target cells 12 or cause damage to the non-target cells 12. Or, thereby inducing a reduction in adhesive force between the non-target cells 12 and the optical fibers 6. In this way, it is possible to remove the non-target cells 12 from the optical fibers 6 in the fiber unit 2. In addition, the non-target cells 12 may be removed by a method different from application of ultraviolet light UV or the like.

Next, as shown in FIGS. 7C and 7D, the target cells 11 are proliferated by use of the fiber unit 2 from which the non-target cells 12 are removed, to form subclones 14 of the target cells 11 (S7). In this case, by removing the non-target cells 12, the optical fibers 6 to which the non-target cells 12 have been attached up to then can be used for proliferating the target cells 11.

Then, in S7 and onward, it is possible to proliferate the target cells 11 by executing S3, S4, and S5 in the same way as in the sorting procedure A.

In this way, in the sorting method according to the sorting procedure B, after the unnecessary non-target cells 12 are removed in S6, a culture is performed to form the subclones 14 in S7. Therefore, only necessary samples preferentially remain in large amounts, and it is possible to perform a culture again at the stage in which the clones become the majority therein (S5). Therefore, distinguishing between the target cells 11 and the non-target cells 12 is clarified, which makes it possible to easily perform sorting of the target cells 11. Accordingly, it is easy to discriminate between the optical fibers 6 (63 and 64) to which the target cells 11 are attached and the optical fibers 6 (61, 62, and 65) to which the non-target cells 12 are attached, which makes it possible to reliably perform separation of the optical fibers 6 in S3.

(Measurement of Optical Characteristics)

Figure 10:
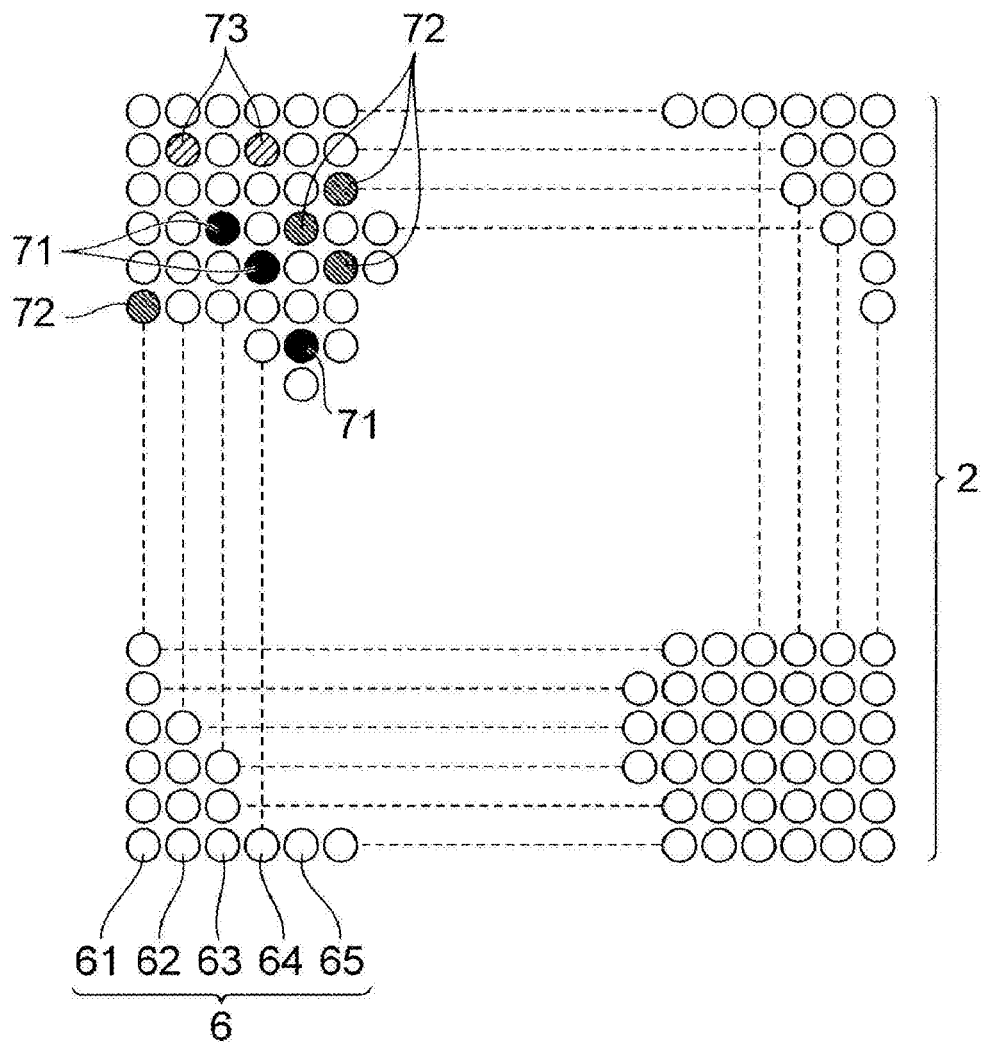
FIG. 10 is a diagram schematically showing an example of optical characteristics of cells by use of the fiber unit.

The measurement of optical characteristics in S3 may be performed as follows, for example. First, a light is applied to the fiber unit 2 from the light source 7, and the transmitted light transmitting through the fiber unit 2 is measured. In this way, for example, as shown in FIG. 10, with respect to the transmitted lights shown by optical fibers 71, 72, and 73, it is possible to separate the optical fibers 6 focusing on the contrasting densities of the respective transmitted lights (the transmitted light of the optical fibers 71 is densest among the optical fibers 71, 72, and 73, and the colors of the transmitted lights become lighter in the order of the optical fibers 71, 72, and 73).

Figure 11:
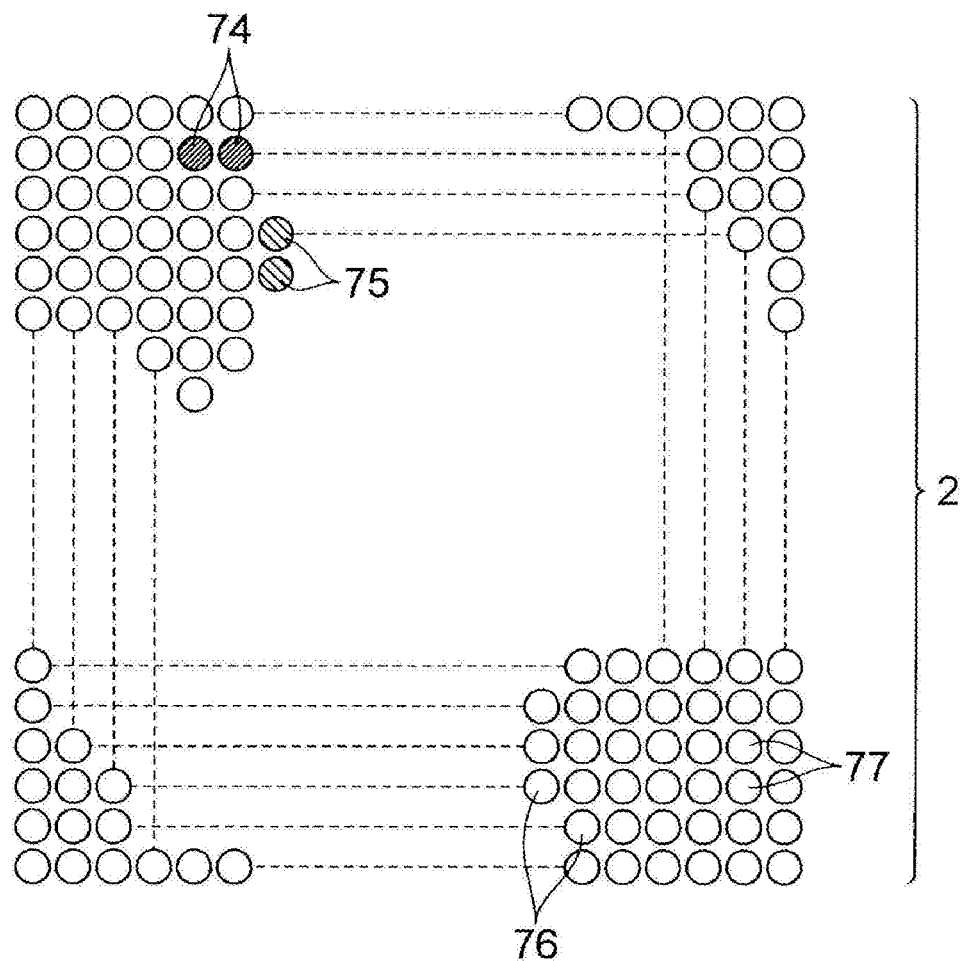
FIG. 11 is a diagram schematically showing another example of optical characteristics of cells by use of the fiber unit.

In addition thereto, the fluorescence or luminescence emitted from the optical fibers may be measured by use of the light source 7a as excitation light. Then, for example, as shown in FIG. 11, it is possible to separate the optical fibers 6 focusing on a difference in color of fluorescence or luminescence emitted from the optical fibers 74 and 75 (the fluorescence from the optical fibers 74 is blue and the fluorescence of the optical fibers 75 is red, and the like).

Figure 13:
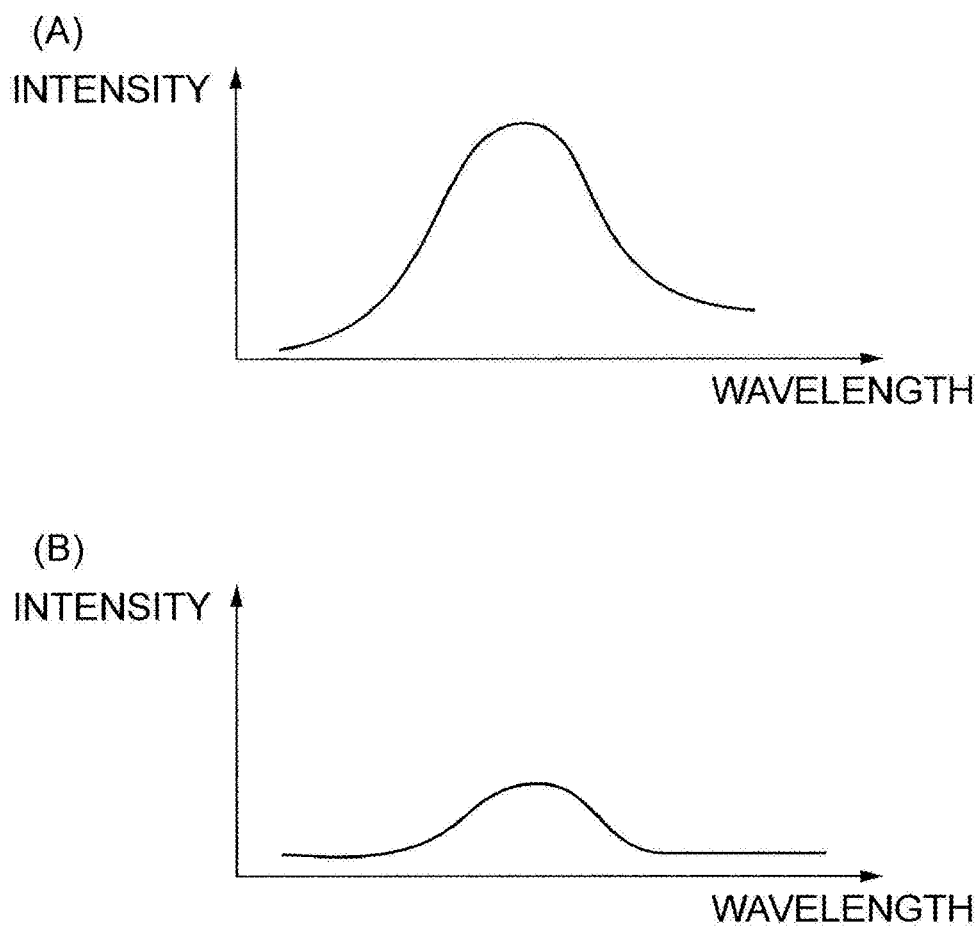
FIG. 13 are graphs schematically showing an example of optical characteristics of cells.

Further, it is possible to separate the optical fibers 6 focusing on a difference in spectrum distribution so that the fluorescence from the optical fibers 76 shows a spectrum distribution in which a particular wavelength is intense as shown in FIG. 13A, and on the other hand, the fluorescence emitted from the optical fibers 77 shows a spectrum distribution which is gentle as a whole as shown in FIG. 13B.

Figure 12:
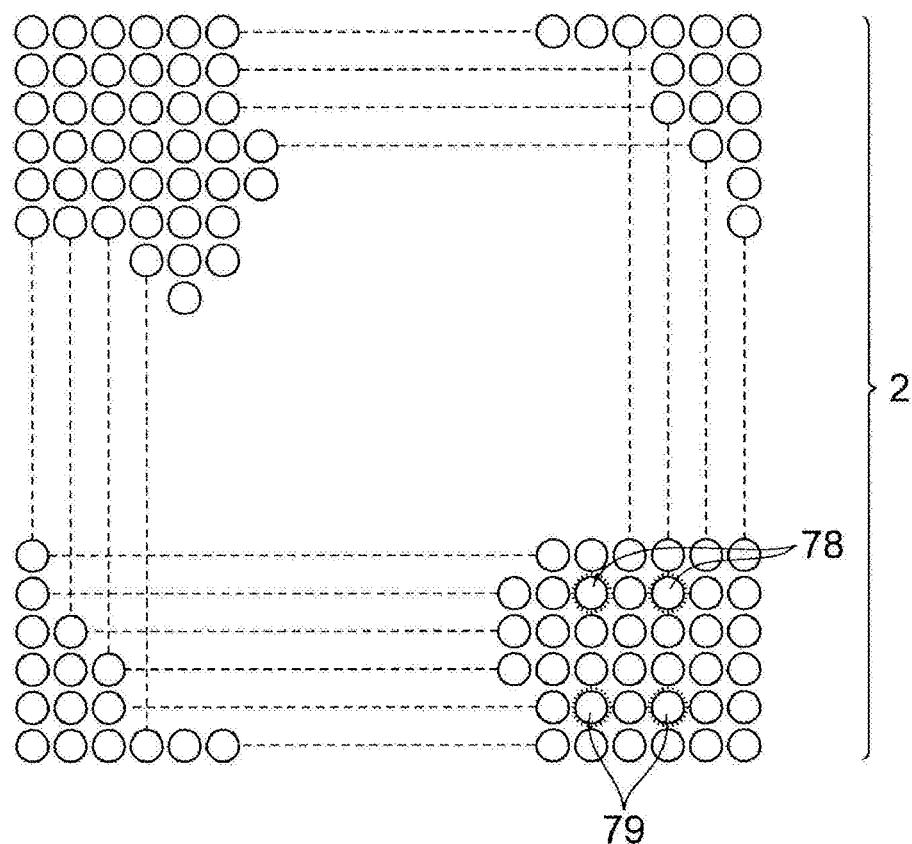
FIG. 12 is a diagram schematically showing yet another example of optical characteristics of cells by use of the fiber unit.
Figure 14:
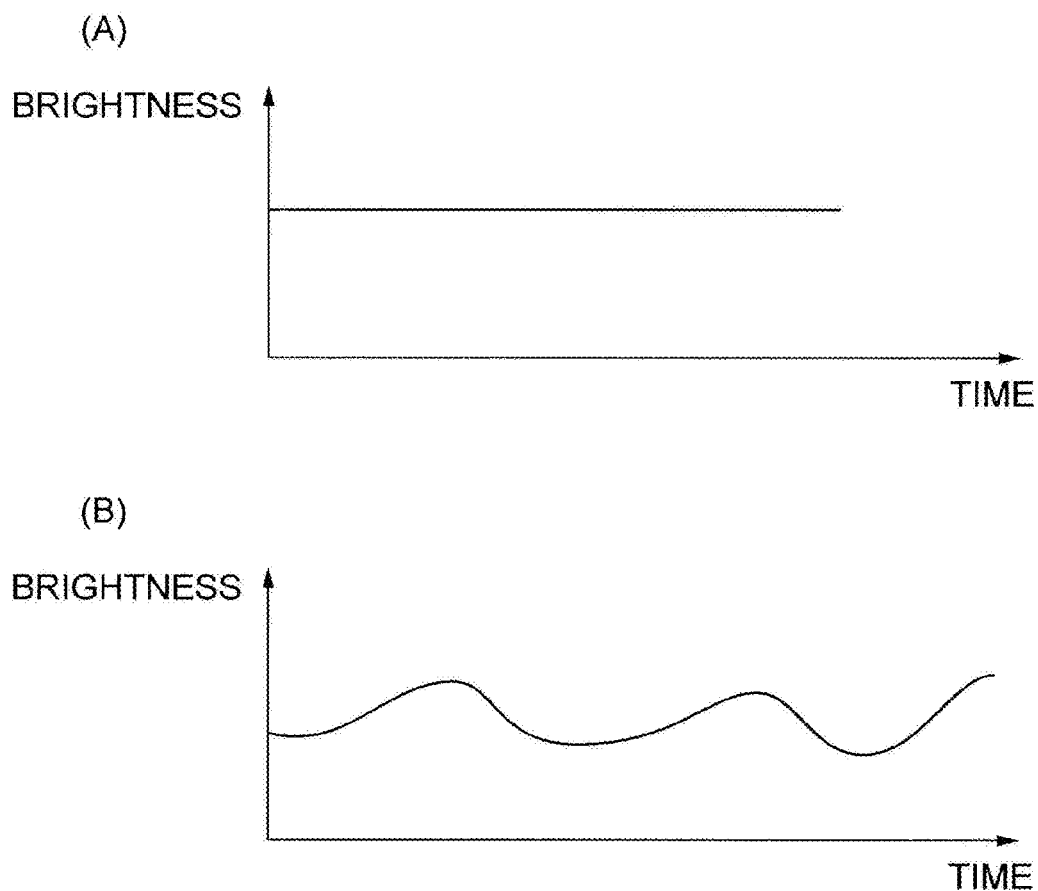
FIG. 14 are graphs schematically showing an example of optical characteristics of cells.

Moreover, the light amounts from the optical fibers may be measured. Then, in this case, as shown in FIG. 12, for example, it is possible to separate the optical fibers 6 focusing on a temporal change in the luminescence emitted from the optical fibers 78 and 79. In this case, for example, the luminescence from the optical fibers 78 has no temporal change but is constant in its brightness as shown in FIG. 14A, and on the other hand, the luminescence from the optical fibers 79 has a temporal change in its brightness as shown in FIG. 14B.

(Modification)

Figure 15:
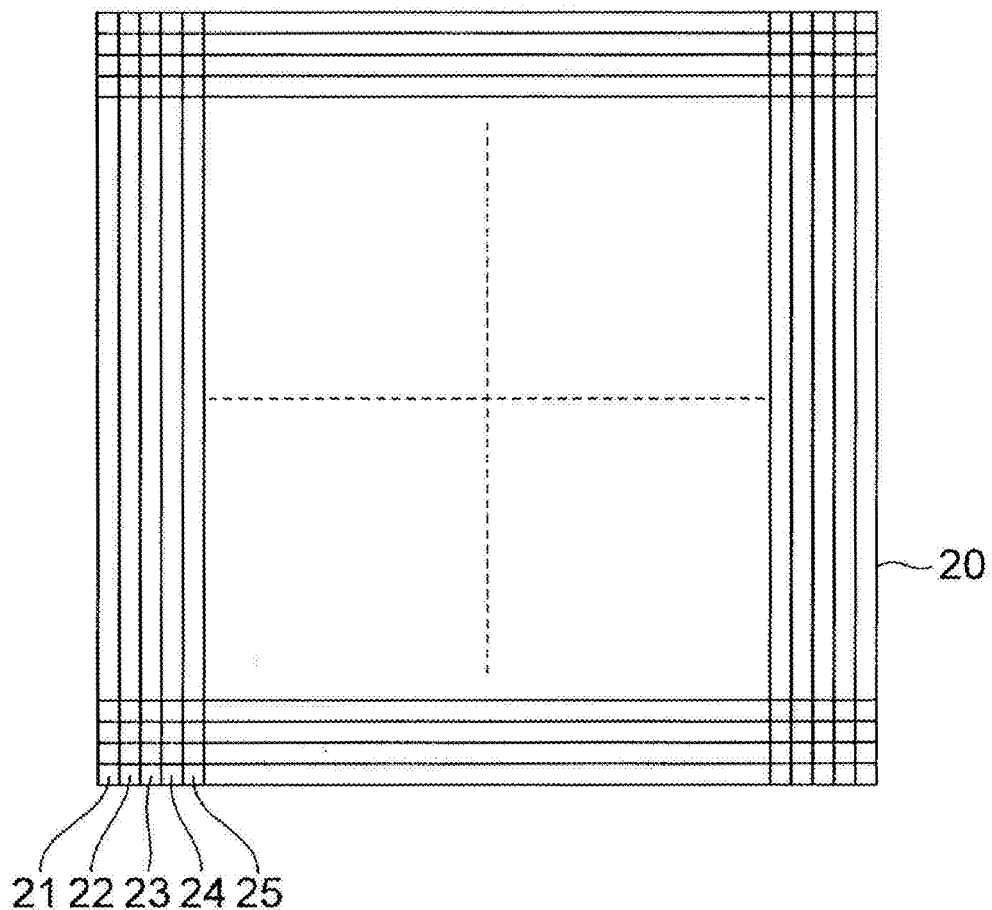
FIG. 15 is a plan view showing an example of a storage case.

In the above-described embodiment, the optical fibers 61, 62, 63, 64, 65, and . . . are integrated with the light-sensitive resin to form the fiber unit 2. However, the optical fibers 61, 62, 63, 64, 65, and . . . may be contained in a storage case 20 as shown in FIG. 15 to form the fiber unit 2.

The storage case 20 has storage cells 21, 22, 23, 24, 25, and . . . having a size in which each of the optical fibers 61, 62, 63, 64, 65, and . . . can be contained, and the height thereof is lower than the optical fibers 6, which allows the entire housing container 20 to be carried as a unit.

By use of the storage case 20, it is easy to align the optical fibers 61, 62, 63, 64, 65, and . . . vertically and horizontally, which makes it easy to handle the fiber unit 2. In addition, provided that coordinates are allocated to the storage cells 21, 22, 23, 24, 25, and . . . , it is possible to specify the coordinates in accordance with the positions of the storage cells. Therefore, it is easy to specify the coordinates of the respective optical fibers 61, 62, 63, 64, 65, and . . . , and it is possible to easily sort the respective optical fibers 61, 62, 63, 64, 65, and . . . .

Moreover, for example, an operation screen for designating coordinates on which a grid according to the storage cells 21, 22, 23, 24, 25, and . . . is formed in a grid pattern is displayed on a display, and images of lights emitted from the optical fibers 61, 62, 63, 64, 65, and . . . are displayed in the corresponding grids on the operation screen. Then, an operator designates a desired grid by an input operation by use of a mouse and/or a keyboard, to make the controller 4 specify a coordinate so as to correspond to the designated grid, and as a result, the coordinate is designated.

Moreover, in the cell sorting method according to the sorting procedure B shown in FIG. 9, S3, S4, and S5 may be not executed after executing S1 to S7. In this case, provided that the removal of the non-target cells 12 in S6 is performed as accurate as possible, to remove the non-target cells 12 as much as possible, it is possible to leave almost only the target cells 11 as cells attached to the fiber unit 2. Thereby, it is possible to proliferate the target cells 11 even if the culture is performed by use of the fiber unit 2 as is, from which the optical fibers 63 and 64 to which the target cells 11 are attached are not separated.

In the fiber unit 2 described above, the coordinates are allocated to the respective optical fibers 6. However, coordinates may not be necessarily allocated to the respective optical fibers 6. However, allocation of coordinates to the respective optical fibers 6 is preferable in the case in which separation of the optical fibers 6 is simply and automatically performed.

Figure 16:
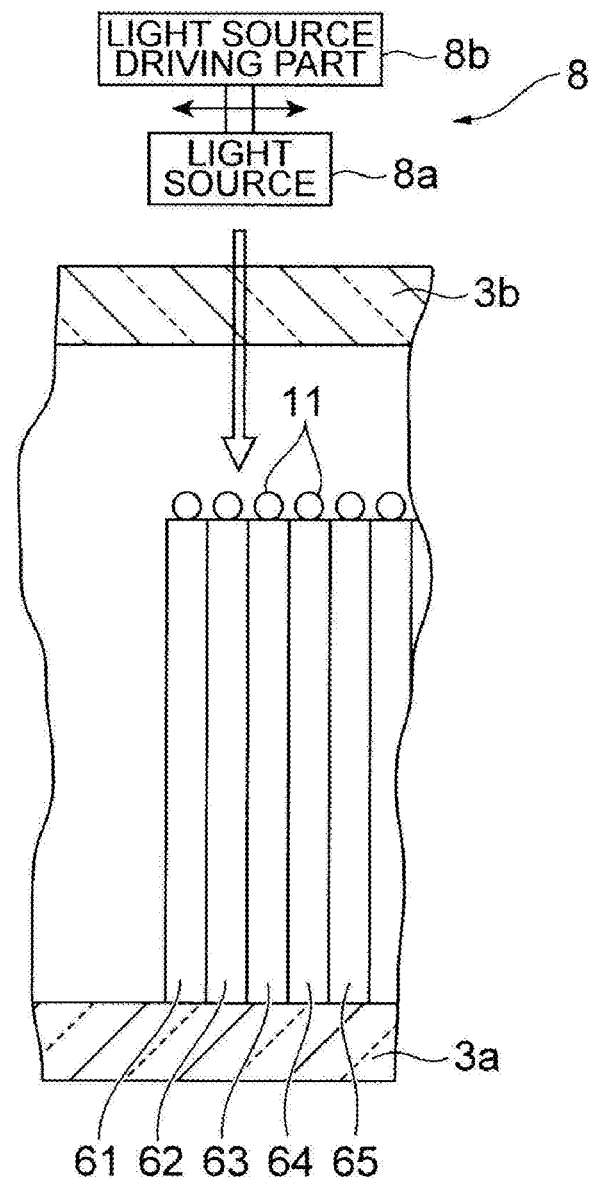
FIG. 16 is a diagram schematically showing a substantial part of the cell sorter of the present invention.

Further, at the time of separating the optical fibers 6 to which target cells are attached, as shown in FIG. 16, a fiber separating part 8 may be provided in the cell sorter 1, and the optical fibers 6 may be automatically separated by the fiber separating part 8. For example, the fiber separating part 8 may be composed of a light source 8a and a light source driving part 8b. The light source 8a applies a light toward the upper side end of the fiber unit 2 to melt the light-sensitive resin on the ends among the optical fibers 6, to separate the optical fibers 6 from each other. In addition, the light source 8a may be composed of a unit in common with the light source 7. The light source driving part 8b moves the light source 8a along the array direction of the optical fibers 61, 62, 63, 64, 65, and . . . , to separate the two desired optical fibers from each other under the control of the controller 4. A beam width of such light applied from the light source 8a is set to, for example, several to several tens of μm so as to be an approximate diameter of the optical fibers 6. When the number of optical fibers to be separated is large, the fiber separating part 8 applies light to a plurality of places on the outermost shell portion of the fiber bundle thereof to separate the fiber bundle collectively. A range of application of light may be enlarged to be approximately a size of the outermost shell portion, to separate the plurality of fibers by one-time application, or the application of light may be divided into several times, to individually separate the plurality of fibers. Here, the controller 4 controls the light source driving part 8b to drive on the basis of the specified coordinates of the optical fibers 63 and 64, which makes it possible to specify the optical fibers 6 to which the target cells 11 are attached, to reliably separate the optical fibers 6.

The above-described description is the description of the embodiment of the present invention, and does not limit the present invention, and various modifications can be easily implemented. Further, an apparatus or a method which is configured by appropriately combining the components, the functions, the features, or the steps of the method in the respective embodiments, are included in the present invention.

INDUSTRIAL APPLICABILITY

In accordance with the cell sorting method and the cell sorter according to the present invention, it is possible to perform sorting focusing on various changes in each cell as stress on living cells is kept as low as possible, and to proliferate the sorted cells.

What is claimed is:

1. A cell sorting method using a fiber bundle unit in which a plurality of fibers are bundled, said fiber bundle unit configured to be separable and unite-able, the cell sorting method comprising the steps of:
dispersing a cell group containing target cells targeted for sorting in a fluid into which the fiber bundle unit is immersed so that said target cells attach to target fibers from among said fibers in said fiber bundle unit;
allowing target cells and non-target cells to attach to the fiber unit,
separating said target fibers from the fiber bundle unit; and
proliferating the target cells by use of the separated target fibers.

2. The cell sorting method according to claim 1, wherein other non-target fibers to which cells are not attached are arranged around the target fibers in the step of proliferating the target cells.

3. The cell sorting method according to claim 1, wherein, before the step of separating the target fibers from the fiber bundle unit, non-target cells are removed from non-target fibers to which non-target cells which are not targeted for sorting are attached or close among the plurality of fibers.

4. The cell sorting method according to claim 1, wherein, before the step of separating the target fibers from the fiber bundle unit, optical characteristics of light of the fiber bundle unit are measured, and the target fiber is separated on the basis of the measured optical characteristics.

5. A cell sorting method using a fiber bundle unit in which a plurality of fibers are bundled, said fiber bundle unit configured to be separable and unite-able the cell sorting method comprising the steps of:
dispersing a cell group containing target and non-target cells targeted for sorting in a fluid into which the fiber bundle unit is immersed, so that said target cells attach to target fibers and said non-target cells attach to non-target fibers from among said fibers in said fiber bundle unit;
separating said non-target fibers from said fiber bundle unit;
allowing target cells and non-target cells to attach to the fiber unit,
removing the non-target cells from said non-target fibers to which non-target cells which are not targeted for sorting are attached; and thereafter,
proliferating the target cells by use of the separated target fibers from said fiber bundle unit.

6. A cell sorting method using a fiber bundle unit in which a plurality of fibers are bundled, the cell sorting method comprising the steps of:
respectively allocating coordinates to the fibers forming the fiber bundle unit;
dispersing a cell group containing target cells targeted for sorting in a fluid into which the fiber bundle unit is immersed;
allowing target cells and non-target cells to attach to target and non-target fibers in the fiber bundle unit designating the coordinates allocated to target fibers to which the target cells are attached among the plurality of fibers;
separating the target fibers whose coordinates are designated, from the non-target fibers in the fiber bundle unit; and
proliferating the target cells by use of the separated target fibers.

7. The cell sorting method according to claim 6, wherein, before the step of designating the coordinates allocated to the target fibers, the non-target cells are removed from non-target fibers to which non-target cells which are not targeted for sorting are attached or close among the plurality of fibers.

8. The cell sorting method according to claim 3, wherein the plurality of fibers are optical fibers, and wherein, in the step of removing the non-target cells from the non-target fibers, a light is applied to the non-target fibers to induce a reduction in adhesive force between the non-target cells and the optical fibers.

9. The cell sorting method according to claim 5, wherein the plurality of fibers are optical fibers, and wherein, in the step of removing the non-target cells from the non-target fibers, a light is applied to the non-target fibers to induce a reduction in adhesive force between the non-target cells and the optical fibers.

10. The cell sorting method according to claim 7, wherein the plurality of fibers are optical fibers, and wherein, in the step of removing the non-target cells from the non-target fibers, a light is applied to the non-target fibers to induce a reduction in adhesive force between the non-target cells and the optical fibers.

11. The cell sorting method according to claim 3, wherein, in the step of removing the non-target cells from the non-target fibers, a light is applied to the non-target fibers to cause damage to the non-target cells or deaden the non-target cells.

12. The cell sorting method according to claim 5, wherein, in the step of removing the non-target cells from the non-target fibers, a light is applied to the non-target fibers to cause damage to the non-target cells or deaden the non-target cells.

13. The cell sorting method according to claim 7, wherein, in the step of removing the non-target cells from the non-target fibers, a light is applied to the non-target fibers to cause damage to the non-target cells or deaden the non-target cells.

* * * * *